US00PP13287P2

(12) United States Plant Patent
Osiecki

(10) Patent No.: US PP13,287 P2
(45) Date of Patent: Nov. 26, 2002

(54) ANTHURIUM PLANT NAMED 'FAVORITA'

(75) Inventor: Marian Wincenty Osiecki, Marianna, FL (US)

(73) Assignee: Oglesby Plants International, Inc., Altha, FL (US)

( * ) Notice: Subject to any disclaimer, the term of this patent is extended or adjusted under 35 U.S.C. 154(b) by 0 days.

(21) Appl. No.: 09/961,829

(22) Filed: Sep. 25, 2001

(51) Int. Cl.[7] ..... A01H 5/00
(52) U.S. Cl. ..... Plt./367

(58) Field of Search ..... Plt./367

*Primary Examiner*—Bruce R. Campell
*Assistant Examiner*—Annette Para

(57) ABSTRACT

A new and distinct cultivar of Anthurium is provided. It is a medium size plant, suitable for production in 15-cm to 20-cm containers, with vigorous growth; full and symmetrical growth habit; early and abundant branching; early, abundant and year-round flowering; and resistance to *Xanthomonas campestris pv. dieffenbachiae*. Exceptionally dark green, relatively large, glossy leaves create a sharp contrast with bright orange-red and glossy spathes held immediately above foliage on straight, strong, relatively thick peduncles.

3 Drawing Sheets

BOTANICAL CLASSIFICATION

Anthurium hybrid.

VARIETY DENOMINATION

'Favorita'.

BACKGROUND OF THE INVENTION

This inventions relates to a new and distinct cultivar of anthurium plant, botanically known as Anthurium hybrid, and hereinafter referred to by the cultivar name Favorita.

The new cultivar is a product of a planned breeding program conducted by the Inventor in Altha, Fla. The objective of the program was to develop a vigorous, well branching pot Anthurium cultivar resistant to *Xanthomonas campestris pv. dieffenbachiae*, with attractive foliage and orange spathes. The new Anthurium was discovered and selected by the Inventor in 1998 as a seedling within the progeny of a cross made in 1995 in a controlled environment in Altha, Fla. The female parent was a proprietary Anthurium seedling selection identified by the code number 91-11-48, obtained by the Inventor in the same breeding program, not patented. The male parent was a selected clone of Anthurium hybrid cultivar Lady Jane identified by the code number 941, not patented.

Asexual propagation of 'Favorita', since 1998, by means of tissue culture in Altha, Fla. has established that the unique characteristics of this new cultivar are in fact stable and reproduced true to type in successive generations.

SUMMARY OF THE INVENTION

The new Anthurium cultivar has not been observed under all possible environmental conditions. The phenotype may vary somewhat with variations in environment and/or horticultural practices such as temperature, light intensity, day length, fertilization, irrigation, propagation procedures etc., without any variance in genotype.

The following traits have been repeatedly observed and in combination distinguish 'Favorita' as a new and distinct cultivar of pot Anthurium:

1. Medium size plant, appropriate for 15-cm to 20-cm containers;
2. Symmetrical, rounded and full growth habit;
3. Vigorous growth;
4. Early and abundant branching;
5. Early, abundant and year-round flowering;
6. Relatively large, glossy and exceptionally dark green leaf blades;
7. Spathes very glossy, orange-red, especially when young, and maintaining color relatively well;
8. Spathes held directly above foliage, on straight, strong and relatively thick peduncles;
9. Resistance to *Xanthomonas campestris pv. dieffenbachiae.*

Plants of 'Favorita' are distinguished from plants of the female parent, a proprietary Anthurium seedling selection identified by the code number 91-11-48, by its smaller size; earlier and more abundant branching; earlier flowering; smaller, darker green and glossier leaf blades; spathes smaller, flatter and more horizontal, held closer to foliage, glossier and orange-red as opposed to dark pink-red spathes of seedling 91-11-48; and straight pink-purple spadices as opposed to curved, dark purple spadices of 91-11-48.

Plants of 'Favorita' are distinguished from plants of the male parent, a selected clone of Anthurium hybrid cultivar Lady Jane identified by the code number 941, by its more vigorous growth, earlier flowering; longer leaf blades; spathes more ovate, wider, with lower length:width ratio, orange-red in color and held above foliage as opposed to dark pink spathes of Lady Jane # 941, often held among foliage; and by pink-purple spadices as opposed to pinkish-cream spadices of Lady Jane #941.

The new cultivar can be compared to its siblings, cultivars: 'Salsa' U.S. Plant patent application Ser. No. 09/960,456 and 'Valentine' U.S. Plant patent application Ser. No. 09/960,455. The comparisons were made on plants of the same age, grown side-by-side under the same greenhouse conditions in Altha, Fla.

Plants of the new Anthurium cultivar differ from plants of the cultivar Salsa in the following characteristics:

1. Plants of 'Favorita' start branching earlier and flower more abundantly than plants of 'Salsa'.

2. Foliage of 'Favorita' is taller than foliage of 'Salsa'.

3. Leaf blades of 'Favorita' are darker green than leaf blades of 'Salsa'.

4. Spathes of 'Favorita' are smaller, held closer to foliage and are orange-red, whereas spathes of 'Salsa' are dark pink-red.

5. Spadices of 'Favorita' are pink-purple, whereas spadices of 'Salsa' are cream-colored.

Plants of the new Anthurium cultivar differ from plants of the cultivar Valentine in the following characteristics:

1. Plants of 'Favorita' are larger, branch less abundantly and have slightly more open growth habit than plants of 'Valentine'.

2. Plants of 'Favorita' start flowering earlier, but flower less abundantly than plants of 'Valentine'.

3. Leaf blades of 'Favorita' are larger, darker green and glossier than leaf blades of 'Valentine'.

4. Peduncles of 'Favorita' are thicker, stronger and longer than peduncles of 'Valentine'.

5. Spathes of 'Favorita' are held closer to foliage, are larger and have shorter longevity on the plant than spathes of 'Valentine'.

6. Spathes of 'Favorita' are orange-red, whereas spathes of 'Valentine' are deep red.

7. Spadices of 'Favorita' are pink-purple, whereas spadices of 'Valentine' are cream-colored.

The new cultivar can be compared to the known Anthurium cultivars: 'Orange Hot', not patented and '75-10', disclosed in U.S. Plant Pat. No. 9,355, a/k/a/ Red Hot™. The comparisons were made on plants of the same age, grown side-by-side under the same greenhouse conditions in Altha, Fla.

Plants of the new Anthurium cultivar differ from plants of the cultivar Orange Hot in the following characteristics:

1. Leaf blades of 'Favorita' are larger and darker green than leaf blades of 'Orange Hot'.

2. Inflorescences of 'Favorita' are of good quality from the onset of flowering, whereas several first spathes produced by plants of 'Orange Hot' are very small and deformed.

3. Spathes of 'Favorita' are held closer to foliage on thicker, stronger and more vertical peduncles than spathes of 'Orange Hot'.

4. Spathes of 'Favorita' are almost horizontal, flat and non-puckered, whereas spathes of 'Orange Hot' are oblique and slightly puckered.

5. Young spathes of 'Favorita' are glossier, have a brighter, more distinct orange-red color than young spathes of 'Orange Hot' and maintain color and gloss longer.

6. Spadices of 'Favorita' are straight, whereas spadices of 'Orange Hot' are usually curved.

Plants of the new Anthurium cultivar differ from plants of the cultivar 75-10 in the following characteristics:

1. Leaf blades of 'Favorita' are larger and darker green than leaf blades of '75-10'.

2. Inflorescenes of 'Favorita' are of a good quality from the onset of flowering, whereas several first spathes produced by plants of '75-10' are very small and deformed.

3. Spathes of 'Favorita' are held closer to foliage on thicker, stronger and more vertical peduncles than spathes of '75-10'.

4. Peduncles of 'Favorita' are brownish green, whereas peduncles of '75-10' are dark purple.

5. Spathes of 'Favorita' are orange-red, almost horizontal, flat and non-puckered, whereas spathes of '75-10' are red, oblique and slightly puckered.

6. Spathes of 'Favorita' maintain color and gloss longer than spathes of '75-10'.

7. Spadices of 'Favorita' are straight and pink-purple, whereas spadices of '75-10' are usually curved and dark purple.

BRIEF DESCRIPTION OF THE PHOTOGRAPHS

The accompanying photographs illustrate the appearance of the new Anthurium cultivar, showing the colors as true as it is reasonably possible in color reproductions of this type. Colors in the photographs may appear slightly different from the color values cited in the botanical description, which accurately describe the actual colors of the plants of the new cultivar. The plant of 'Favorita' depicted in the photographs was approximately 15 months from planting a single tissue culture-produced microcutting, and was grown in a 15-cm container.

In the photographs:

BOTANICAL DESCRIPTION OF THE NEW CULTIVAR

Figure 1:
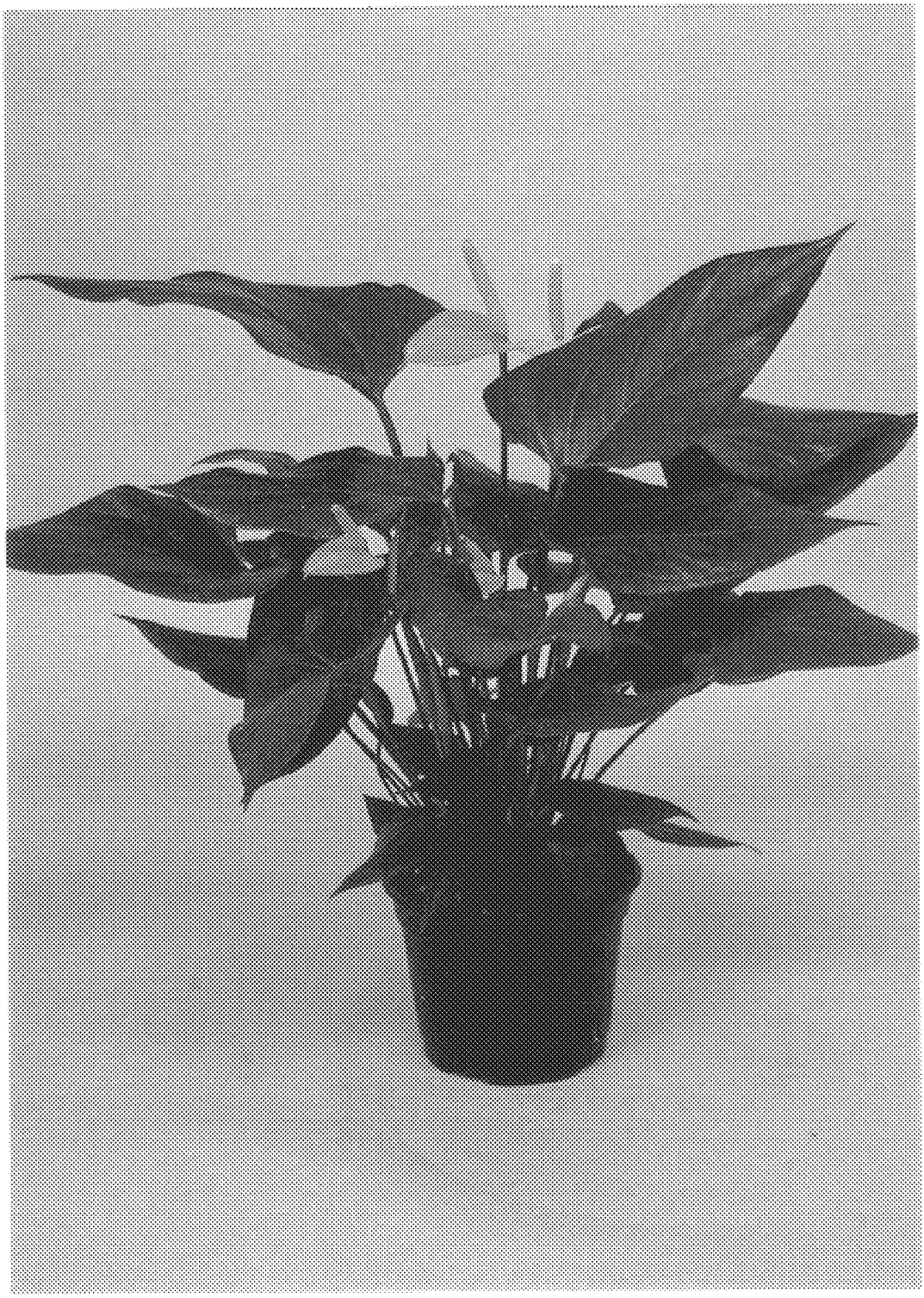
FIG. 1 depicts the whole plant.
Figure 2:
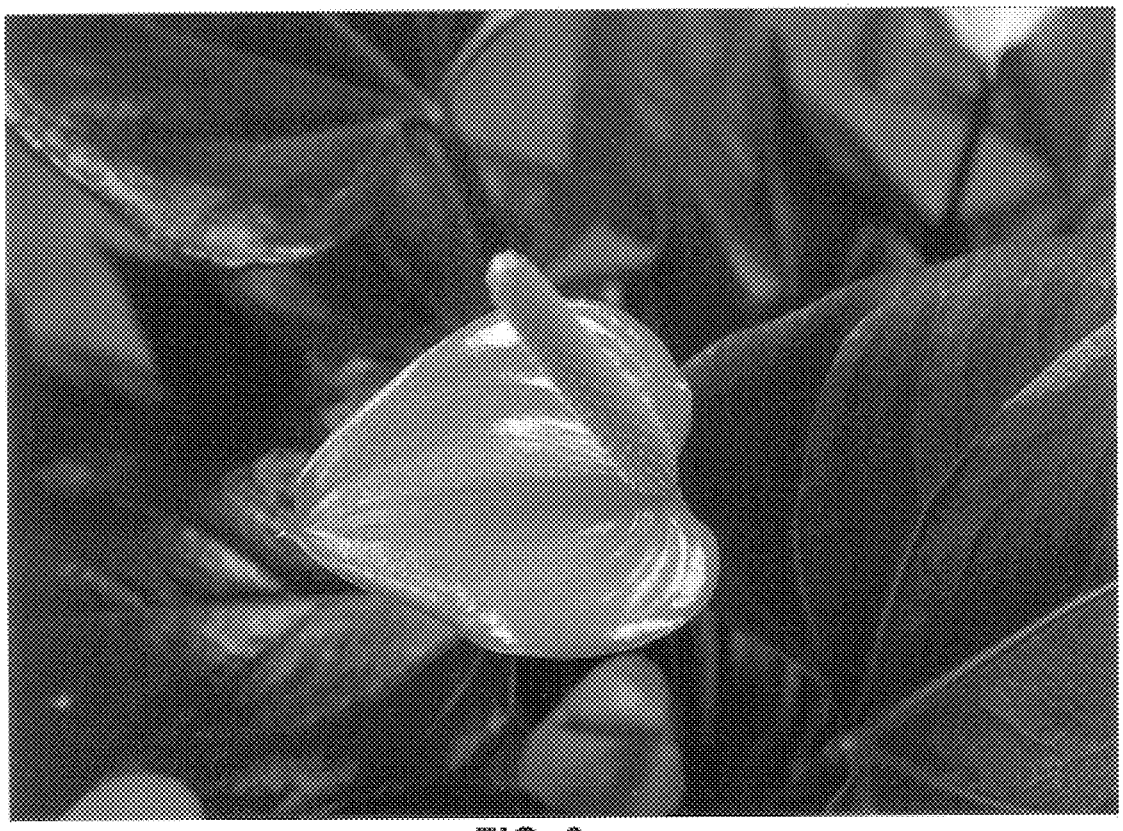
FIG. 2 illustrates the mature inflorescence.
Figure 3:
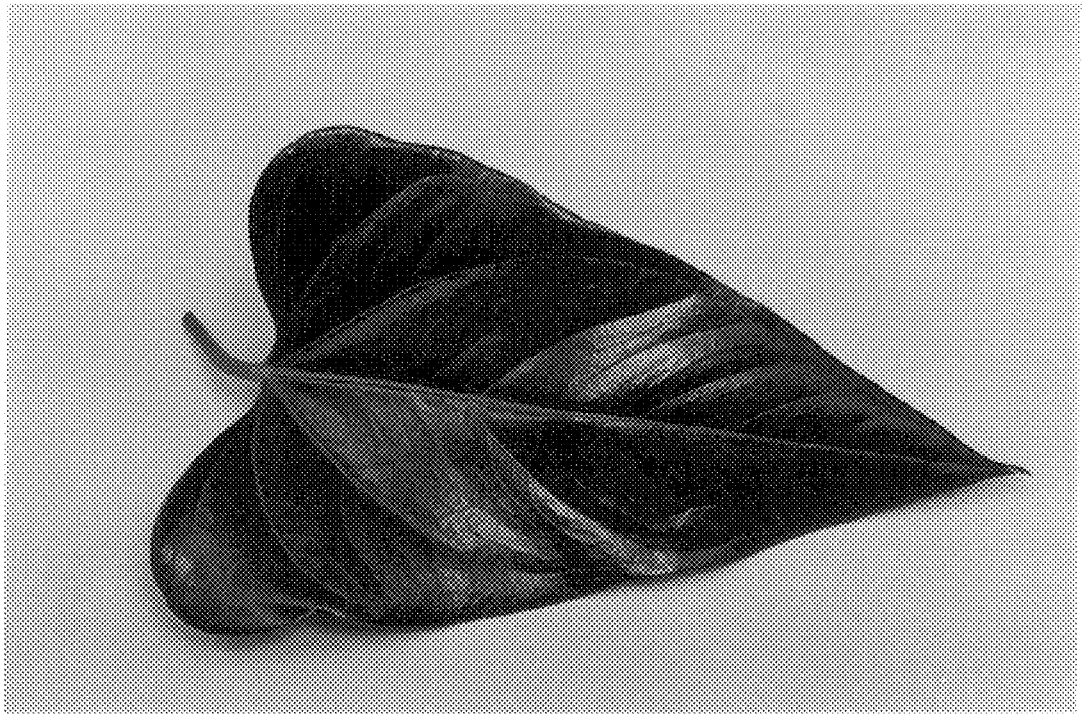
FIG. 3 illustrates the adaxial side of a mature leaf.
Figure 4:
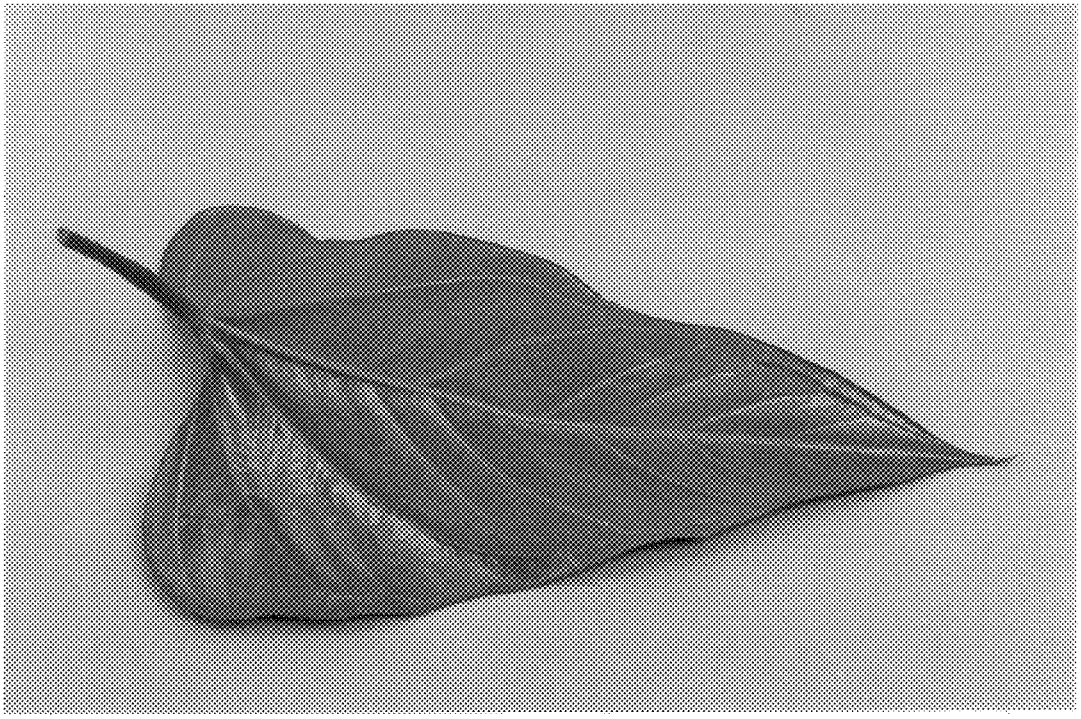
FIG. 4 illustrates the abaxial side of a mature leaf.

The following observations and measurements were recorded in February and March 2001, on plants grown in a polycarbonate-covered greenhouse in Altha, Fla. under conditions which closely approximate those used in commercial horticultural practice. During growth of these plants day temperature in the greenhouse ranged between 23 and 28° C., night temperature ranged between 20 and 23° C., and light level ranged between 800 and 1500 foot-candles. Plants used for these observations were grown as single plants in 15-cm containers and were about 15 months from planting tissue culture-produced microcuttings.

Mature, fully developed plants were used for the following observations and measurements unless otherwise indicated. Numerical measurements represent means from typical plants of 'Favorita'. Color references are made to The R.H.S. Colour Chart, except where general color terms of ordinary significance are used. Color values were determined under natural light of approximately 860 to 2000 foot-candles.

Botanical classification: Anthurium hybrid cultivar Favorita.
Parentage:

*Female parent.*—Proprietary Anthurium seedling selection identified by the code number 91-11-48 (not patented).

*Male parent.*—Selected clone of Anthurium hybrid cultivar Lady Jane, identified by the code number 941 (not patented).

Propagation:

*Type.*—Plant tissue culture.

*Time to produce a rooted liner.*—Summer: About 13 to 14 weeks at about 25 to 30° C. soil temperature. Winter: About 15 to 16 weeks at about 22 to 27° C. soil temperature.

Plant description:

*Growth habit.*—Medium size, rounded, symmetrical, well-branched, full. Appropriate for 15-cm to 20-cm containers.

*Plant size.*—Height, soil level to top of inflorescences: About 39.2 cm. Height, soil level to top of leaf canopy: About 35.9 cm.

*Diameter* (*area of spread*).—About 51.6 cm.

*Plant vigor.*—Vigorous.

*Crop time.*—About twelve months are needed to produce a finished plant in a 15-cm container from a single tissue culture-produced microcutting.

Foliage description:

*Petiole.*—Size: About 24.6 cm long, about 4.6 mm in diameter immediately below geniculum. Geniculum: About 3.0 cm long, about 5.2 mm in diameter at the base. Not very prominent. Color: Newly unrolled leaf, adaxial: Between 144A and 146A. Geniculum approximately 146A. Newly unrolled leaf, abaxial: Slightly darker than 144A. Mature leaf, adaxial: Varies between different combinations of 146A and 144A with distally increasing amounts of purplish anthocyanin coloration. Mature leaf, abaxial: Varies between different combinations of 146A, 146B and 144A, sometimes with some purplish anthocyanin coloration. Geniculum varies between different combinations of 146A and 144A.

*Leaf blade.*—Shape: Ovate; apex long, acuminate; base between cordate and truncate; margin entire. Size: About 23.4 cm long, about 15.0 cm wide; length: width ratio about 1.6:1. Aspect: Most leaves approximately horizontal; some slightly oblique with apices pointing up; lobes curving upwards. Texture/surface: Thick, leathery, glabrous, glossy; young leaves very glossy. Venation: Pinnipalmate; prominent primary veins. Color: Newly unrolled leaf, adaxial: Between 147A and 146A, exceptionally glossy. Most of midrib and proximal portions of primary veins between 146A and 144A. Newly unrolled leaf, abaxial: Approximately 146A. Midrib approximately 144A. Mature leaf, adaxial: Exceptionally dark green. Looks almost black beside the closest color, 147A. Most of midrib and proximal portions of primary veins approximately 146A with some purplish anthocyanin coloration near petiole juncture. Mature leaf, abaxial: Similar to or slightly greener than 146A. Most of midrib and proximal portions of primary veins approximately 146A with slight purplish anthocyanin coloration near petiole juncture.

Inflorescence description:

*Inflorescence arrangement.*—Most spathes with spadices held immediately above foliage. Peduncles almost vertical, straight, strong, relatively thick. Most mature spathes approximately horizontal. Most spadices at approximately 70–80° angle with spathe.

*Flowering.*—Abundant and year-round. Flowers naturally in 15-cm containers about 9 months after planting tissue culture-produced microcuttings. At 15 months about 6.4 inflorescences per plant, including buds.

*Spathe longevity.*—In spring spathe maintains color and gloss for approximately 2.5 months following bud appearance.

*Peduncle.*—Size: About 31.2 cm long, about 3.9 mm in diameter immediately below spathe. About 4.5 mm of peduncle between spathe and spadix base in front. Stipe up to 1 mm long. Color: Just before spathe unrolling, front: Similar to 146A near base with increasing amount of orange-brown anthocyanin coloration in distal half. Immediately below spathe varies between different combinations of 172B, 175C, 166B, 166C and 164A, sometimes with some addition of green. Just before spathe unrolling, back: Similar to 146A near base. The amount of orange-brown anthocyanin coloration increases distally. Varies between 172A, 172B and 34B near spathe. Mature inflorescence, front: Similar to or darker than 146A with increasing amount of orange-brown anthocyanin coloration in the distal half. Similar to or darker than 34B immediately below spathe base. Approximately 34A between spathe base and spadix base. Mature inflorescence, back: Similar to 146A near base. The amount of orange-brown anthocyanin coloration increases distally.

*Spathe.*—Shape: Ovate; apex between acuminate and aristate; base cordate; margin entire. Size: About 6.7 cm long, about 5.5 cm wide; ratio length:width about 1.2:1. Texture/Surface: Glabrous; exceptionally glossy; sometimes slightly puckered. Color: Closed bud (before unrolling): Varies between different combinations of 41A, 41B, 44D, 43B and a color lighter than 34A. Newly unrolled spathe, front surface: Varies between different combinations of the following colors: 33A, 34A, a color lighter than 34A, 41A, 43B, 44C. A fine line along the margin darker than 34A. With age spathe becomes less orange. Newly unrolled spathe, back surface: Uneven color. Usually darkest in the central zone along midrib (similar to 44D or a color lighter than 44D). Lighter towards margins (39B or a color lighter than 39B). Midrib approximately 44B to 44C. Mature spathe, front surface: Varies between different combinations of 39A, 42C, 44C, 41A, 41B and a color lighter than 34A, but is closest to 39A. A fine line along margin darker than 34A. Mature spathe, back surface: Uneven color. Usually darkest in the central zone near midrib (similar to 44D or a color lighter than 44D). Usually lighter towards margins (lighter than 39B, but darker than 39C). Midrib approximately 44B.

*Spadix.*—Shape: Cylindrical, straight, very slightly tapering at apex; cross section rounded. Size: About 5.6 cm long, about 10.4 mm in diameter. Flower density: About 15 to 16 flowers per linear 2 cm of spadix (mid-section). Color: Young, immediately after spathe unrolling: Near base, where pistils start emerging, between 51B and a color darker than 48A. Distally merges with 39A or a color darker than 39A. Mature inflorescence: Proximal zone, with pistils, 51C or darker than 51C. Distally merges with 39A or a color darker than 39A in the zone without pistils.

*Botanical flower.*—Perianth: Perianth of an individual flower appears on the spadix surface as almost a diamond shape, about 2.5 to 3 mm long and 2 to 2.5 mm wide. Pistil: About 2.1 mm long and about 1.3 mm in diameter; protrudes fraction of a millimeter beyond perianth; cream-colored, translucent with a pink ring on the circumference. Stigma small. Stamens: About 1.3 mm long and 0.8 mm wide; cream-colored, translucent; flat; firmly pressed against pistil; do not protrude beyond perianth until pollen dehiscence. Pollen: Aging inflorescences produce moderate amounts of whitish pollen. Fragrance: Weak to moderate, pleasant fragrance detectable in the morning.

*Seed.*—Spontaneous seed development not observed.

Roots description: Thick, fleshy main roots, cream-colored with yellow root caps. Abundant, relatively thick, cream-colored lateral roots.

Disease and insect resistance: Plants of 'Favorita', which are grown in commercial greenhouses, have not shown any unusual susceptibility to pathogens or insects common to Anthurium. In the greenhouse tests plants of 'Favorita' have demonstrated high degree of resistance to *Xanthomonas campestris pv. dieffenbachiae.*

I claim:

1. A new and distinct cultivar of Anthurium plant named 'Favorita' as described and illustrated herein.

* * * * *